US005455006A

United States Patent [19]
Aota et al.

[11] Patent Number: 5,455,006
[45] Date of Patent: Oct. 3, 1995

[54] SAMPLE CONTAINER TURNING APPARATUS

[75] Inventors: Kensaku Aota, Hyogo; Kunio Ishikawa, Akashi; Jun Toyoda, Kobe; Souichi Tani, Kakogawa, all of Japan

[73] Assignee: TOA Medical Electronics Co., Ltd., Hyogo, Japan

[21] Appl. No.: 289,561

[22] Filed: Aug. 12, 1994

[30] Foreign Application Priority Data

Aug. 17, 1993 [JP] Japan .................................. 5-203467

[51] Int. Cl.⁶ .................................................. G01N 35/02
[52] U.S. Cl. .............................. 422/63; 422/65; 422/100; 422/103; 422/104; 436/47; 436/43
[58] Field of Search ................................ 422/63, 65, 64, 422/103, 104, 100, 99; 436/43, 47, 48

[56] References Cited

U.S. PATENT DOCUMENTS

| | | | |
|---|---|---|---|
| 4,478,095 | 10/1984 | Bradley et al. | 73/864.21 |
| 4,582,990 | 4/1986 | Stevens | 250/328 |
| 4,595,562 | 6/1986 | Liston et al. | 422/65 |
| 4,927,545 | 5/1990 | Roginski | 210/745 |
| 4,951,512 | 8/1990 | Mazza et al. | 73/861.23 |
| 5,008,082 | 4/1991 | Shaw | 422/65 |
| 5,158,895 | 10/1992 | Ashihara et al. | 436/526 |
| 5,209,903 | 5/1993 | Kanamori et al. | 422/65 |

FOREIGN PATENT DOCUMENTS

| | | |
|---|---|---|
| 263425 | 7/1968 | Austria . |
| 255026 | 3/1988 | European Pat. Off. . |
| 479622 | 8/1992 | European Pat. Off. . |

Primary Examiner—James C. Housel
Assistant Examiner—Long V. Le

[57] ABSTRACT

A sample container turning apparatus including: a holding member for holding a plurality of sample containers in a predetermined direction; an intermittent conveyor for conveying the holding member intermittently; an arm member; a rotary member rotatably mounted on the arm member; a hand member attached to the rotary member and including a plurality of grip hands hinged to the rotary member so as to pivot on hinge shafts for gripping and releasing the one of the sample containers; a couple member coupled to the hand member and including a shaft member adapted to reciprocate through the rotary member; a first drive mechanism for pivoting the hand members by reciprocating the shaft member of the coupling member; a second drive mechanism for rotating the rotary member; and controller for controlling the first drive mechanism and the second drive mechanism. The hand member is pivoted by the first drive mechanism and the coupling member to cause its plurality of grip hands to grip the one sample container, and the rotary member is then rotated by the second drive mechanism to turn the one sample container on its axis.

8 Claims, 6 Drawing Sheets

SAMPLE CONTAINER TURNING APPARATUS

BACKGROUND OF THE INVENTION

1. Field of the Invention

The present invention relates to a sample container turning apparatus and, more particularly, to a sample container turning apparatus for turning a sample container (or specimen container) containing a sample (or specimen) such as blood to be analyzed, on the axis of the container with a view to reading the code of a bar code label adhering to the container, or mixing and homogenizing the sample in the container.

2. Description of the Prior Art

In the prior art, there is an automatic analyzing system for analyzing a specimen by conveying a plurality of specimen containers to a specimen analyzing apparatus. In this system, there has been widely used a specimen rack for holding the specimen containers generally vertically so as to hold and convey the containers.

The specimen container held by the specimen rack may sometimes be desired to be turned on the generally vertical axis of the container. This occurs, for example, when the specimen in the container is agitated so that it may be homogenized or when the code of the bar code label adhering to the specimen container is read out. The following examples are known in the prior art as the specimen container turning apparatus for turning the specimen container held on the specimen rack on the generally vertical axis of the container.

One example is a specimen container turning apparatus which is constructed such that there is vertically movably provided a rotary member made rotatably on a vertical axis, such that the rotary member is lowered from above a specimen container closed with a cap, onto the upper face of the cap of the specimen container, and such that the rotary member is then rotated. In the specimen container turning apparatus thus constructed, the rotary member transmits its rotational force to the specimen container by a frictional force which is generated by a pressure contact between the rotary member and the cap of the specimen container.

Another example is a specimen container turning apparatus which is constructed like the aforementioned turning apparatus excepting that the rotary member has its lower face bulged or recessed whereas the specimen container has its upper face recessed or bulged to be fitted on the lower face of the rotary member. In the specimen container turning apparatus thus constructed, the rotary member transmits its rotational force to the specimen container by the fitting contacts of the recessed and bulged portions of the rotary member and the specimen container.

In the former specimen container turning apparatus, when the rotary member is forced to contact the upper face of the cap of the specimen container, the frictional force is generated between the bottom wall of the specimen container and the container holding face of the specimen rack. The frictional force thus generated may act as a resistance at the turning time to make the turn of the specimen container insufficient.

This problem grows especially serious when a rubber sheet or the like is applied to the container holding face of the specimen rack so as to prevent any unnecessary turn of the specimen container when the code of the bar code label adhering to the specimen container held by the specimen rack is read out. In order to solve this problem, a high torque has to be given to the drive source used for the rotary member.

In the latter specimen container turning apparatus, on the other hand, in order to fit the rotary member and the specimen container snugly, it is necessary to provide a mechanism for positioning the rotary member and the specimen container precisely. For this necessity, there arises a problem that the turning apparatus is enlarged in size and the mechanism thereof becomes more complicated.

The present invention has been conceived in view of the background thus far described and an object of the invention is to provide a small-sized simple sample container turning apparatus capable of transmitting the turning force reliably from a drive source to a sample container even the drive source used has a low torque.

SUMMARY OF THE INVENTION

According to the present invention, there is provided a sample container turning apparatus comprising: a holding member for holding a plurality of sample containers in a predetermined direction; intermittent conveyor means for conveying the holding member intermittently; an arm member; a rotary member rotatably mounted on the arm member; a hand member attached to the rotary member and including a plurality of grip hands hinged to the rotary member so as to pivot on hinge shafts for gripping and releasing one of the sample containers; coupling means coupled to the hand member and including a shaft member adapted to reciprocate through the rotary member; first drive means for pivotting the hand members by reciprocating the shaft member of the coupling means; second drive means for rotating the rotary member; and control means for controlling the first drive means and the second drive means, wherein the hand member is pivotted by the first drive means and the coupling means to cause its plurality of grip hands to grip the one sample container, and wherein the rotary member is then rotated by the second drive means to turn the one sample container on its axis.

The sample container used is, for example, a sample container composed of a container body having a test tube shape, or a sample container composed of a container body and a cap made of rubber or plastics and fitted in the upper opening of the container body. The holding member is exemplified by a sample rack for holding ten sample containers generally vertically in a row. This holding member is intermittently conveyed by intermittent conveyor means such as a belt conveyor of an intermittent motion type.

The arm member is generally horizontally arranged over the sample rack generally vertically holding the sample containers. The rotary member rotates the sample container. The hand member is composed of two grip hands which are adapted to pivot on horizontal hinge shafts, for example. These grip hands are pivotted to grip and release the sample container (the container body or the cap). The shaft member of the coupling means is vertically reciprocated, for example. The first drive means used is exemplified by having an air cylinder or a solenoid. The second drive means used is exemplified by having a motor and a rotation transmitting member. The rotations of the rotary member of the second drive means may preferably be switched back and forth. The control means used is equipped with a microcomputer, a RAM and a ROM.

The hand member may preferably be constructed in the following manner. Specifically, the hand member may preferably be constructed such that its plurality of grip hands are pivotted to have their leading ends closer to each other when they grip one sample container.

The hand member may more preferably be constructed in the following manner. Specifically, the hand member may more preferably be composed of: slots loosely fitted on the hinge shafts; and a carriage integrated with the shaft member of the coupling means for carrying the grip hands through the slots in the moving direction of the shaft member when the shaft member moves to pivot the grip hands in the gripping direction.

In the initial state, the hand member is positioned apart from the sample container held by the holding member. First of all, the holding member holding the sample containers is intermittently conveyed by the intermittent conveyor means until the holding member stops at a predetermined position. After this, the first drive means is activated to transmit its driving force to the hand member through the coupling means. Then, the hand member is pivotted on its hinge shafts toward the one sample container into a closed state to grip the one sample container.

Next, in this state, the second drive means is activated to rotate the rotary member. Together with the rotary member, moreover, the hand member gripping the one sample container is rotated to turn the sample container on its axis. As the case may be, the direction of this rotation is reversed at a predetermined time interval. As the sample container is turned, the code of the bar code label adhering to the sample container is read, or the sample in the sample container is agitated that it is homogenized.

Here, in the case where the hand member is so constructed that the hand member is pivotted to allow the plurality of grip hands thereof to come closer to each other at their leading end when the grip hands grip the one sample container, the hand member acts in the following manner. Specifically, if the sample containers has an elastic part, the elastic part of one sample container is elastically deformed when it is gripped by the grip hands of the hand member. At the same time, the hand member is pivotted to allow the plurality of grip hands thereof to come closer to each other at their leading ends so that the sample container is moved to leave the container holding face of the holding member. In other words, the sample container can be slightly lifted. When the sample container has a non-elastic part gripped by the grip hands of the hand member, the hand member may have their grip hands made of an elastic member at their inner sides (abutting against the cap). Incidentally, the elastic part of sample container is a cap formed of, for example, an elastic material such as rubber or the like. The non-elastic part is a cap or a container body formed of, for example, a non-elastic material such as hard plastic or the like.

On the other hand, the hand member acts in the following manner when it is equipped with: slots loosely fitted on the hinge shafts; and a carriage integrated with the shaft member of the coupling means for carrying the grip hands through the slots in the moving direction of the shaft member when the shaft member moves to pivot the grip hands in the gripping direction. Specifically, after the grip hands of the hand member have gripped the one sample container, the carriage is activated to release the sample container from the holding face of the holding member. In other words, the sample container can be lifted.

When the action of the second drive means ends to stop the turn of the sample container, the action of the first drive means ends to restore the aforementioned initial state.

According to the present invention, because of the construction thus far described, the sample containers are not forced onto their holding member unlike the prior art, but it is possible to provide a small-sized simple sample container turning apparatus capable of transmitting the turning force reliably from a drive source to a sample container even the drive source used has a low torque.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE PREFERRED EMBODIMENTS

The present invention will be described in detail in the following in connection with two embodiments with reference to the accompanying drawings.

EMBODIMENT 1

Figure 1:
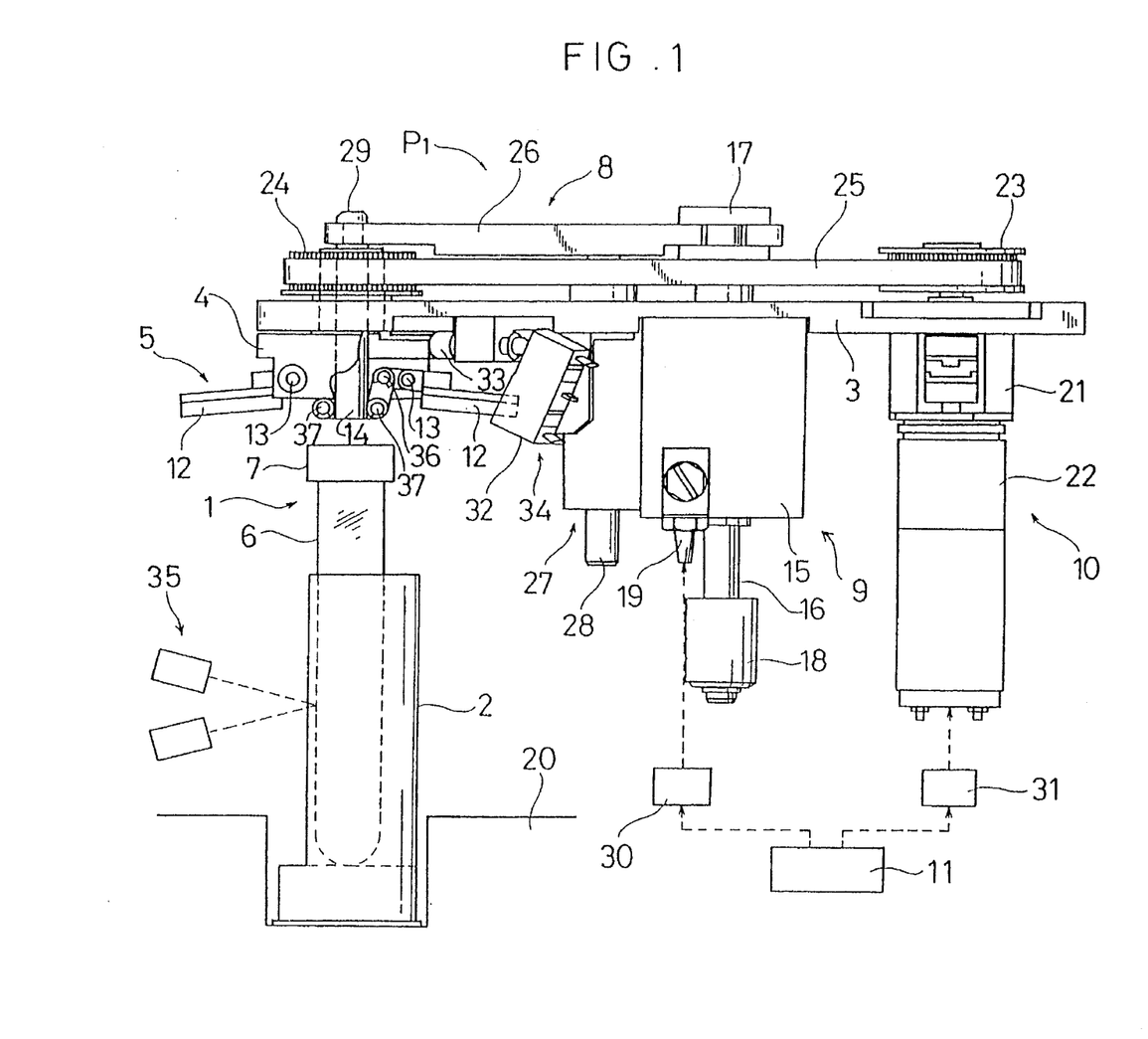
FIG. 1 is an explanatory diagram showing a construction of a sample container turning apparatus according to Embodiment 1 of the present invention at a first stage of its operating state.

In FIG. 1, a sample container turning apparatus P1 is constructed to include: a sample rack 2 acting as a holding member for generally verticaly holding a plurality of sample containers 1; a belt conveyor of an intermittent motion type 20 acting as intermittent motion means; an arm member 3 arranged generally horizontally over the sample containers 1; a rotary member 4 so attached to the lower side of the lefthand end portion of the arm member 3 as to rotate on a vertical axis of rotation; a hand member 5 attached so coaxially to the rotary member 4 as to rotate together; coupling means 8 connected to the hand member 5; first drive means 9 for pivotting the hand member 5 through the joint means 8; second drive means 10 for rotating the rotary member 4; and control means 11 for controlling the first drive means 9 and the second drive means 10.

The belt conveyor 20 conveys the sample rack 2 holding the sample containers 1 intermittently. Each sample container 1 is composed of a test tube like container body 6 filled with blood to be analyzed, and a rubber cap 7 fitted in the upper opening of the container body 6 for sealing the opening. A bar code label containing varied information adheres to the container body 6. The sample rack 2 is formed into a test tube stand for holding ten sample containers 1 generally vertically in a row.

The hand member 5 is equipped with two opposed grip hands 12 and 12, which are so coaxially mounted on the rotary member 4 as to rotate together with the rotary member 4. At the same time, the grip hands 12 and 12 can vertically pivot on horizontal hinge shafts 13 and 13 so as to grip and release the cap 7 of the sample containers 1. The hand member 5 is further equipped with two kinds of hinge pins 36 and 37 which are arranged in parallel with the hinge shafts 13 and 13. By these hinge pins 36 and 37 and hinge shafts 13 and 13, the hand member is pivotted to allow the two grip hands 12 and 12 to come closer to each other at their leading ends when the grip hands grip the cap 7 of the sample container 1.

The first drive means 9 is composed of an air cylinder 15 which is attached to the lower face of the central portion of the arm member 3. The cylinder rod 16 of the air cylinder 15 moves up and down. A joint 17 is attached to the upper end of the cylinder rod 16 whereas a stopper 18 is attached to the lower end of the cylinder rod 16. The air cylinder 15 is provided with an air inlet/output port 19 on its circumferential wall. In the body of the air Cylinder 15, there is vertically disposed a (not shown) compression spring for urging the cylinder rod 16 downward at all times.

The second drive means 10 is composed of: a motor 22 having a vertical shaft and mounted on the lower face of the righthand end portion of the arm member 3 through a mounting member 21; a first pulley 23 fixed on the shaft of the motor 22; a second pulley 24 disposed at a lefthand side of and at a predetermined distance from the first pulley 23 and integrated with the rotary member 4; and a belt 25 horizontally tensed to run on the first pulley 23 and the second pulley 24. The rotation direction of the motor 22 is reversed at a predetermined time interval.

The coupling means 8 is composed of a flat bar 26 which is generally horizontally arranged over the arm member 3. The flat bar 26 has its righthand end fixed to the joint 17 and its lefthand end fixed to a vertical holding rod 29 and has its lower face attached at its righthand portion to a guide rod 28 of a guide member 27. The holding rod 29 is fitted through the rotary member 4 in a vertical shaft member 14 which can vertically reciprocate. Moreover, the flat bar 26 of the coupling means 8 is guided to move up and down by the guide rod 28 as the cylinder rod 16 of the first drive means 9 moves up and down. The grip hands 12 and 12 of the hand member 5 are opened to their maximum stroke when the flat bar 26 takes its lowermost position, as shown in FIG. 1.

The control means 11 is composed of a microcomputer, a RAM and a ROM for controlling an air cylinder drive circuit 30 and a motor drive circuit 31.

Referring to FIG. 1, reference numeral 34 designates rotation detecting means which is composed of a switch unit 32 and a detection unit 33. This rotation detecting means 34 is provided for stopping the rotary member 4 in a predetermined rotational position. On the other hand, numeral 35 designates a bar code reader, by which is read the code of the bar code label adhered to the container body 6 of the sample container 1.

There will be described hereinbelow the operations of the sample container turning apparatus P1 thus constructed.

As shown in FIG. 1, the sample rack 2 holding sample containers 1 is intermittently conveyed and stopped to a predetermined position (i.e., just below the rotary member 4) by the belt conveyor 20. After this, the first drive means 9 is activated to transmit its driving force to the hand member 5 through the shaft member 14 of the coupling means 8. Then the hand member 5 are pivotted on the hinge shafts 13 and 13 toward the cap 7 of one sample container 1 to allow the two grip hands 12 and 12 to come into a closed state to grip the cap 7.

Figure 2:
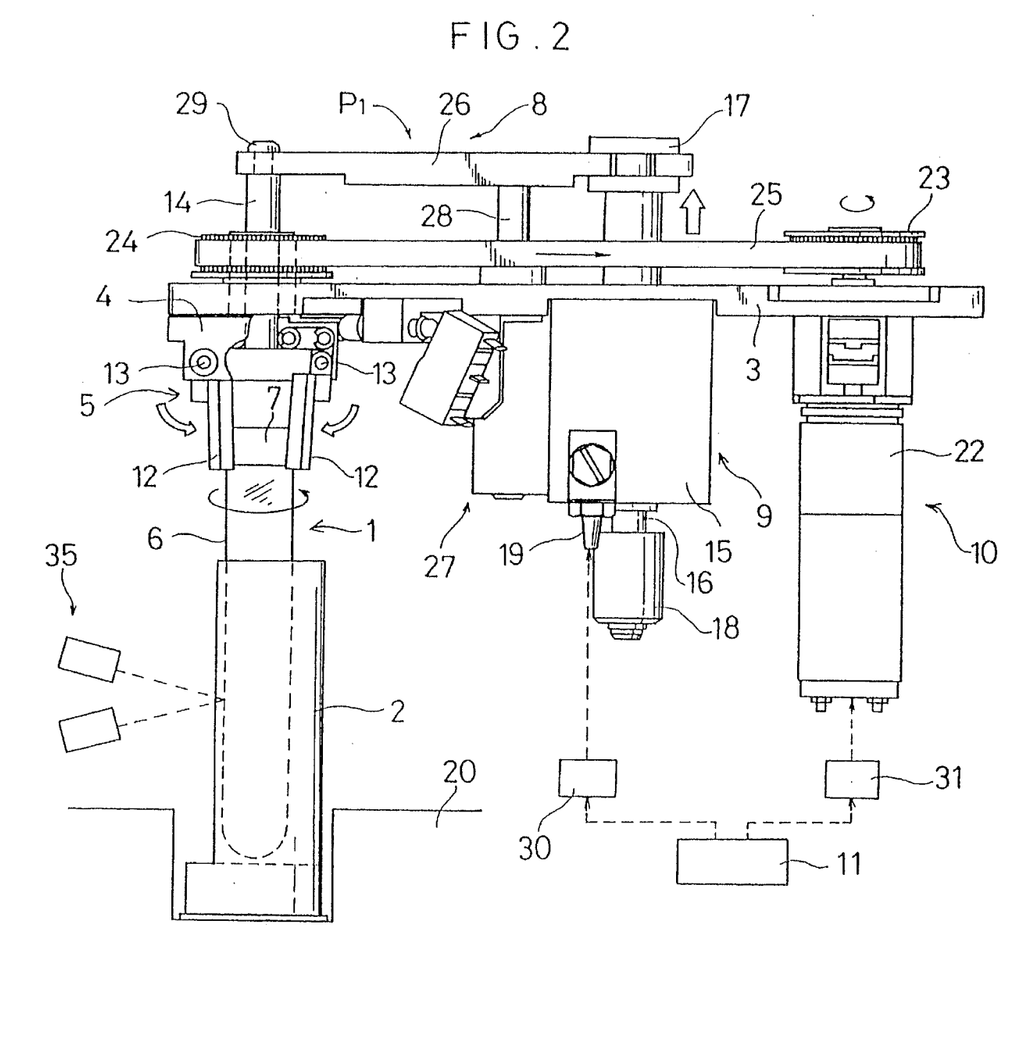
FIG. 2 is an explanatory diagram showing the construction at a second stage of the operating state of the sample container turning apparatus.

Here, the hand member 5 is constructed so that the hand member 5 is pivotted to allow the two grip hands 12 and 12 to come closer to each other at their leading ends when the two grip hands 12 and 12 grip the cap 7 of the sample container 1, as described hereinbefore. Moreover, the cap 7 is made of rubber. As a result, the cap 7 is elastically deformed, as shown in FIG. 2, when it is gripped by the grip hands 12 and 12, and the hand member 5 is pivotted to allow the grip hands 12 and 12 thereof to come closer to each other at their leading ends to lift the sample container 1 slightly (e.g., 1 to 2 mm) from the container holding face of the sample rack 2.

In this state, the motor 22 of the second drive means 10 is then actuated to rotate the rotary member 4 forward by one turn. This rotational speed is set to about 3 to 7 seconds so as to read the bar code. Then, the hand member 5 gripping the cap 7 is rotated together with the rotary member 4 to turn the sample container 1 forward on its axis through the cap 7. By this forward turn of the sample container 1, the code of the bar code label adhering to the container body 6 of the sample container 1 is read by the bar code reader 35. Incidentally, the sample container 1 may be then turned backward by one turn in order to read the bar code again when imaging that the code cannot be read because the bar code label is partially turned up or caught by the sample rack 2.

Thus, the sample container 1 is turned forward and backward while slightly floating above the container holding face of the sample rack 2. As a result, no frictional resistance is generated between the sample container 1 and the sample rack 2 so that the sample container 1 can smoothly turn.

The motor 22 of the second drive means 10 is not stopped till the sample container 1 makes one turn in each of the forward and backward directions. Then, the cylinder rod 16 of the first drive means 9 lowers to the lowest position so that the grip hands 12 and 12 of the hand member 5 release the cap 7 of the sample container 1 having finished its turns through the coupling means 8. Subsequently, the sample container 1 is intermittently conveyed through the sample rack 2 by the belt conveyor 20.

In the sample container turning apparatus P1 thus far described, the sample container 1 having its cap 7 gripped by the hand member 5 is turned forward and backward while being slightly lifted from the container holding face of the sample rack 2. As a result, no frictional resistance between the sample container 1 and the sample rack 2 is generated to smoothen the rotation of the sample container 1. Thus, according to the sample container turning apparatus P1, even if the drive source used has a low torque, there can be provided the small-sized simple sample container turning apparatus, in which the rotational force is transmitted without fail from the drive source to the sample container 1 to turn the container 1 to a sufficient extent.

Figure 3:
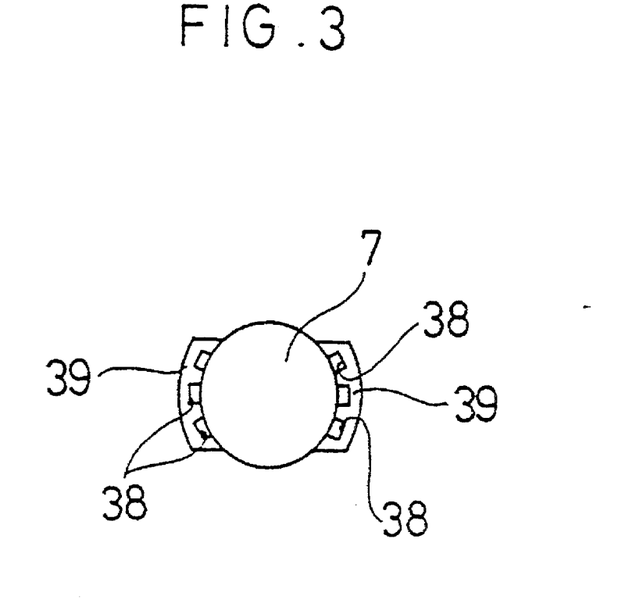
FIG. 3 is an explanatory diagram showing a construction of Modification 1 of a hand member of the sample container turning apparatus.
Figure 4:
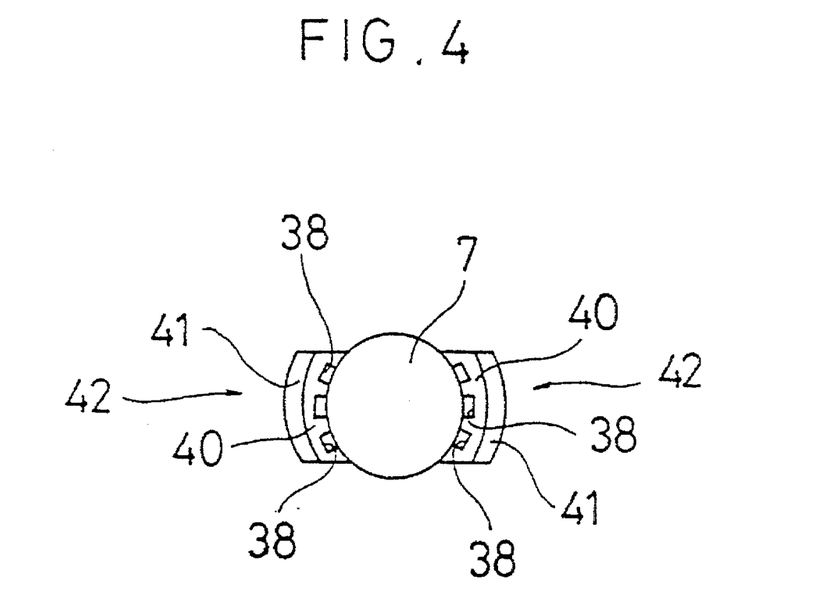
FIG. 4 is an explanatory diagram showing a construction of Modification 2 of the hand member of the sample container turning apparatus.

Incidentally, the grip hands 12 and 12 of the hand member 5 of the sample container turning apparatus P1 are made of an aluminum alloy and have their inner faces smoothly curved. However, these grip hands 12 and 12 may be replaced by aluminum alloy grip hands 39 and 39 which are individually formed with three longitudinal grooves 38, 38 and 38 in their inner faces, as shown in FIG. 3. Alternatively, as shown in FIG. 4, the grip hands 12 and 12 may be replaced by grip hands 42 and 42 which are prepared by adhering rubber grip portions 40 and 40 having the three longitudinal grooves 38, 38 and 38 in their inner faces to support portions 41 and 41. Because of these modifications, it is possible to make the gripping action of the cap 7 more reliable and to prevent the cap 7 from sticking to the grip hands 39 and 39, and 42 and 42.

EMBODIMENT 2

Figure 5:
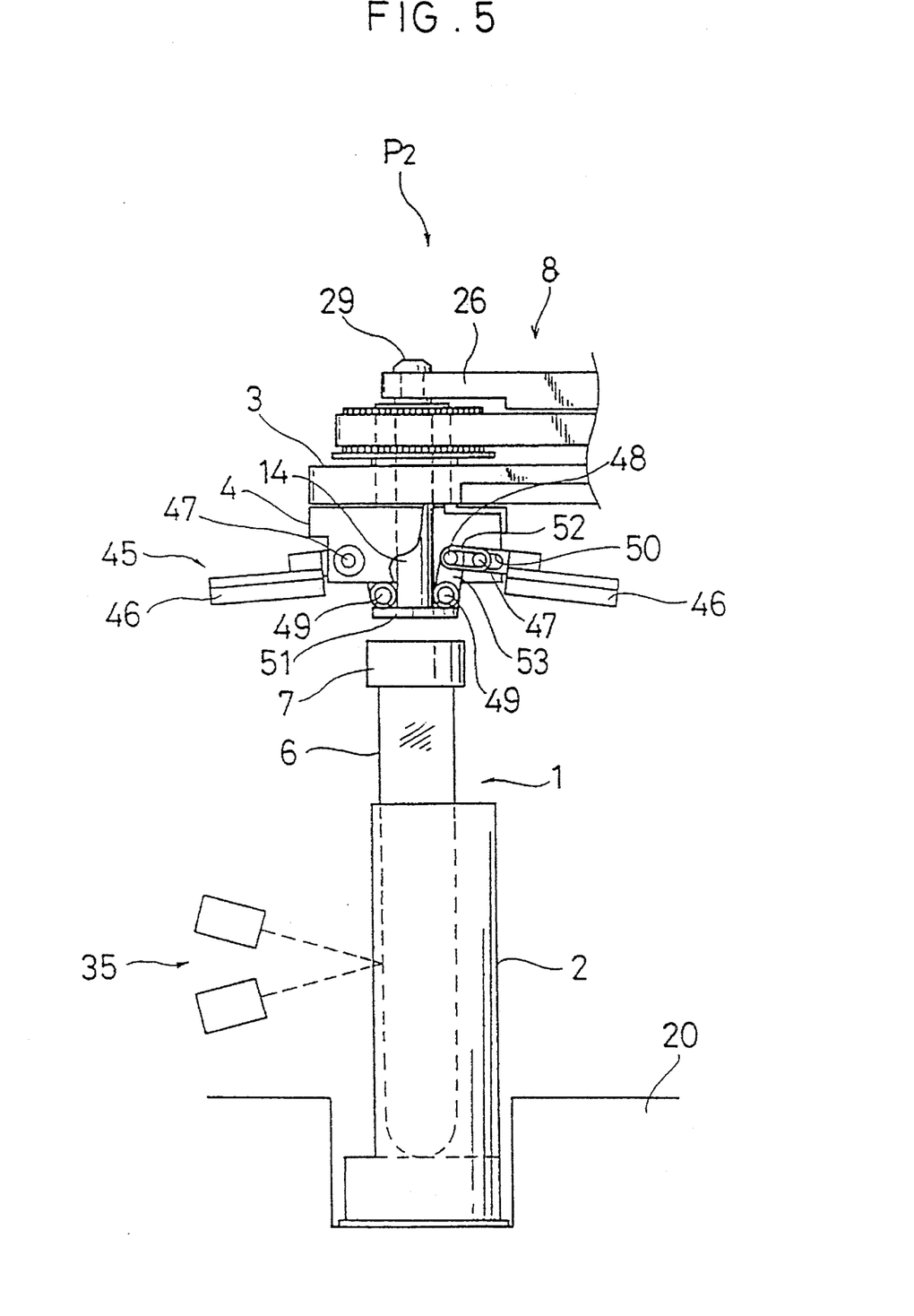
FIG. 5 is an explanatory diagram showing a construction of a sample container turning apparatus according to Embodiment 2 of the present invention at a first stage of its operating state.

In FIG. 5, a sample container turning apparatus $P_2$ is constructed to include: the sample rack 2 acting for generally vertically holding the plurality of sample containers 1; the belt conveyor 20; the arm member 3; the rotary member 4; a hand member 45 attached so coaxially to the rotary member 4 as to rotate together; the coupling means 8 connected to the hand member 45; the first drive means 9 for pivotting the hand member 45 through the joint means 8; the second drive means 10 for rotating the rotary member 4; and the control means 11.

The sample containers 1, the sample rack 2, the belt conveyor 20, the arm member 3, the rotary member 4, the coupling means 8, the first drive means 9, the second drive means 10 and the control means 11 are identical to those of Embodiment 1. Moreover, the bar code reader 35 is also identical to that of Embodiment 1.

The hand member 45 is equipped with two opposed grip hands 46 and 46, which are so coaxially mounted on the rotary member 4 as to rotate together with the rotary member 4. At the same time, the grip hands 46 and 46 can vertically pivot on horizontal hinge shafts 47 and 47 so as to grip and release the cap 7 of the sample containers 1. The hand member 45 is further equipped with: an elliptical slot 50 fitted with a play on each of the hinge shafts 47; and a plate-shaped carriage 51 integrated with the shaft member 14 of the coupling means 8 for carrying the individual grip hands 46 through the slots 50 in the moving direction of the shaft member 14 when the shaft member 14 moves to pivot the individual grip hands 46 in the gripping direction.

The hand member 45 is further equipped with two kinds of hinge pins 48 and 49 which are arranged in parallel with the hinge shafts 47 and 47. The two kinds of hinge pins 48 and 49 are anchored on front and rear two generally elliptical flat bars 53. Moreover, the hinge pins 49 near the carriage 51 are anchored on the (not shown) bearing member which is integrated with the carriage 51. By these hinge pins 48 and 49 and hinge shafts 47 and 47, the hand member 45 is pivotted to allow the two grip hands 46 and 46 to grip the cap 7 of the sample container 1.

One end of each of the two flat bars 53 is in abutment against each end portion of the upper face of the carriage 51. Front and rear two rubber rings 52 are forced to run on the individual hinge shafts 47 and the hinge pins 48 near the former. These rubber rings 52 bias the individual hinge shafts 47 and the near hinge pins 48 to have a predetermined distance at all times.

There will be described hereinbelow the operations of the sample container turning apparatus $P_2$ thus constructed.

As shown in FIG. 5, the sample rack 2 holding sample containers 1 is intermittently conveyed and stopped to a predetermined position (i.e., just below the rotary member 4) by the belt conveyor 20. After this, the first drive means 9 is activated to transmit the driving force to the hand member 45 through the shaft member 14 of the coupling means 8. Then the hand member 45 is pivotted on the hinge shafts 47 and 47 toward the cap 7 of one sample container 1 to allow the two grip hands 46 and 46 thereof to come into a closed state to grip the cap 7.

Figure 7:
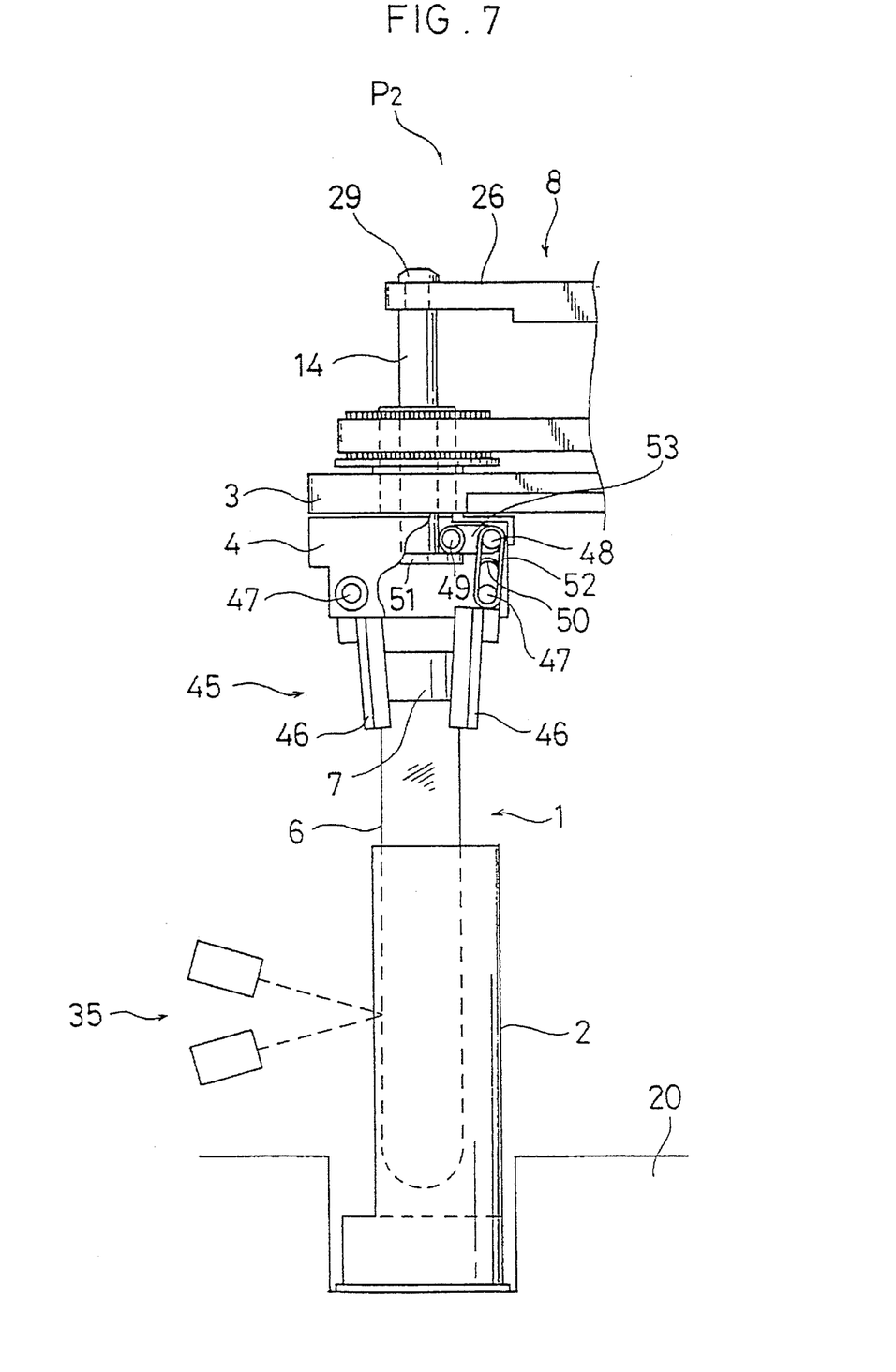
FIG. 7 is an explanatory diagram showing the construction at a third stage of the operating state of the sample container turning apparatus.

Next, as shown in FIG. 7, the shaft member 14 of the coupling means 8 in this state is further lifted by the first drive means 9. As the carriage 51 of the hand member 45 is then lifted by the shaft member 14 of the coupling means 8, the flat bars 53 are accordingly lifted. Then, the individual grip hands 46 are lifted accordingly with the rise of the flat bars 53 by the actions of the slots 50 which are loosely fitted on the individual hinge shafts 47. As a result, the sample container 1 is lifted by (e.g., 3 to 4 mm) from the container holding face of the sample rack 2. This lifting actions of the individual grip hands 46 are ended when the hinge shafts 47 come to the lower ends of the slots 50. At this time, the individual rubber rings 52 are in the extended states.

In this state, the motor 22 of the second drive means 10 is then actuated to rotate the rotary member 4 forward by one turn. This rotational speed is set to about 3 to 7 seconds per one turn. Then, the hand member 45 gripping the cap 7 is rotated together with the rotary member 4 to turn the sample container 1 forward on its axis through the cap 7. By this forward turn of the sample container 1, the code of the bar code label adhering to the container body 6 of the sample container 1 is read by the bar code reader 35. Incidentally, the sample container 1 is then turned backward by one turn while imaging that the code cannot be read because the bar code label is partially turned up or caught by the sample rack 2.

Thus, the sample container 1 is turned forward and backward while floating above the container holding face of the sample rack 2. As a result, no frictional resistance is generated between the sample container 1 and the sample rack 2 so that the sample container 1 can smoothly turn.

The motor 22 of the second drive means 10 is not stopped till the sample container 1 makes one turn in each of the forward and backward directions. Then, the cylinder rod 16 of the first drive means 9 lowers to the lowest position so that the grip hands 46 and 46 of the hand member 45 release the cap 7 of the sample container 1 having finished its turns through the coupling means 8. Subsequently, the sample container 1 is intermittently conveyed through the sample rack 2 by the belt conveyor 20.

In the sample container turning apparatus $P_2$ thus far described, the sample container 1 having its cap 7 gripped by the hand member 45 is turned forward and backward while being lifted from the container holding face of the sample rack 2. As a result, no frictional resistance between the sample container 1 and the sample rack 2 is generated to smoothen the rotation of the sample container 1. Thus, according to the sample container turning apparatus $P_2$, even if the drive source used has a low torque, there can be provided the small-sized simple sample container turning apparatus, in which the rotational force is transmitted without fail from the drive source to the sample container 1 to rotate the container 1 to a sufficient extent.

Figure 6:
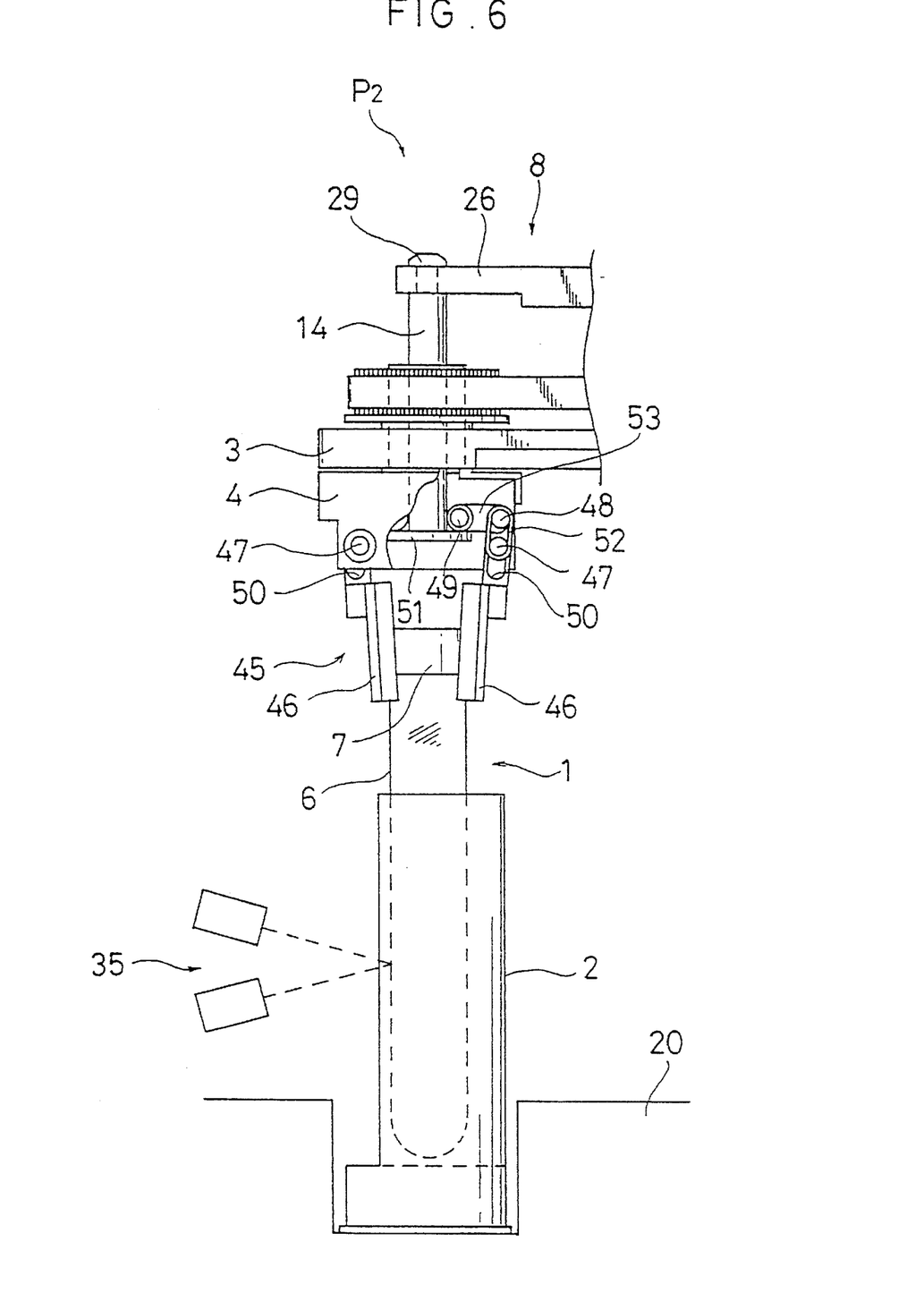
FIG. 6 is an explanatory diagram showing the construction at a second stage of the operating state of the sample container turning apparatus.

Here, the hand member 45 may be constructed so that the hand member 45 is pivotted to allow the two grip hands 46 and 46 to come closer to each other at their leading ends when they grip the cap 7 of the sample container 1, as described hereinbefore. Moreover, the cap 7 may be made of rubber. As a result, the cap 7 is elastically deformed, as shown in FIG. 6, when it is gripped by the grip hands 46 and 46, and the grip hands 46 and 46 of the hand member 45 are pivotted to have their leading ends brought closer to each other to lift the sample container 1 slightly (e.g., 1 to 2 mm) from the container holding face of the sample rack 2.

Incidentally, the grip hands 46 and 46 of the hand member 45 of the sample container turning apparatus $P_2$ are made of an aluminum alloy and have their inner faces smoothly curved. However, these grip hands 46 and 46 may be replaced by the grip hands 39 and 39, as shown in FIG. 3, or the grip hands 42 and 42, as shown in FIG. 4. Because of these modifications, it is possible to make the gripping action of the cap 7 more reliable and to prevent the cap 7 from sticking to the grip hands 39 and 39, and 42 and 42.

What is claimed is:

1. A sample container turning apparatus comprising: a holding member for holding a plurality of sample containers in a predetermined direction; intermittent conveyor means for conveying said holding member intermittently; an arm member; a rotary member rotatably mounted on said arm member; a hand member attached to said rotary member and including a plurality of grip hands hinged to said rotary member so as to pivot on hinge shafts for gripping and releasing one of said sample containers; coupling, means coupled to said hand member and including a shaft member which reciprocates through said rotary member; first drive means for pivoting said hand members by reciprocating the shaft member of said coupling means; second drive means for rotating said rotary member; and control means for controlling said first drive means and said second drive means, wherein said hand member is pivoted by said first drive means and said coupling means to cause said plurality of grip hands to grip said one sample container, and wherein said rotary member is then rotated by said second drive means to turn said one sample container on an axis;

wherein said hand member includes: slots loosely fitted on said hinge shafts; and a carriage integrated with the shaft member of said coupling means for carrying said grip hands through said slots in the moving direction of said shaft member when said shaft member moves to pivot said grip hands in a gripping direction.

2. A sample container turning apparatus according to claim 1, wherein the shaft member of said coupling means is generally vertically reciprocated.

3. A sample container turning apparatus according to claim 1, wherein said first drive means includes an air cylinder attached to said arm member.

4. A sample container turning apparatus according to claim 1, wherein said second drive means includes: a motor mounted on said arm member; and a rotation transmitting member for transmitting the rotation of said motor.

5. A sample container turning apparatus according to claim 1, wherein the rotations of said rotary member by said second drive means can be switched back and forth.

6. A sample container turning apparatus according to claim 1, wherein said control means includes a microcomputer, a RAM and a ROM.

7. A sample container turning apparatus comprising: a holding member for holding a plurality of sample containers in a predetermined direction; intermittent conveyor means for conveying said holding member intermittently; an arm member; a rotary member rotatably mounted on said arm member; a hand member attached to said rotary member and including a plurality of grip hands hinged to said rotary member so as to pivot on hinge shafts for gripping and releasing one of said sample containers; coupling means coupled to said hand member and including a shaft member which reciprocates through said rotary member; first drive means for pivoting said hand members by reciprocating the shaft member of said coupling means; second drive means for rotating said rotary member; and control means for controlling said first drive means and said second drive means, wherein said hand member is pivoted by said first drive means and said coupling means to cause said plurality of grip hands to grip said one sample container, and wherein said rotary member is then rotated by said second drive means to turn said one sample container on an axis wherein the sample containers or inner sides of the grip hands of said hand member have an elastic part so that said elastic part is elastically deformed whereas said hand member is pivoted to allow said plurality of grip hands to come closer to each other at leading ends of said grip hands when said hand member is pivoted by said first drive means and said coupling means to cause said plurality of grip hands to grip said one sample container.

8. A sample container turning apparatus, comprising: a holding member for holding a plurality of sample containers in a predetermined direction; intermittent conveyor means for conveying said holding member intermittently; an arm member; a rotary member rotatably mounted on said arm member; a hand member attached to said rotary member and including a plurality of grip hands hinged to said rotary member so as to pivot on hinge shafts for gripping and releasing one of said sample containers; coupling means coupled to said hand member and including a shaft member which reciprocates through said rotary member; first drive means for pivoting said hand members by reciprocating the shaft member of said coupling means; second drive means for rotating said rotary member; and control means for controlling said first drive means and said second drive means, wherein said hand member is pivoted by said first drive means and said coupling means to cause said plurality of grip hands to grip said one sample container, and wherein said rotary member is then rotated by said second drive means to turn said one sample container on an axis wherein said hand member includes: slots loosely fitted on said hinge shafts; and a carriage integrated with the shaft member of said coupling means for carrying said grip hands through said slots in the moving direction of said shaft member when said shaft member moves to pivot said grip hands in a gripping direction, and wherein the grip hands of said hand member are pivoted to grip the cap of said one sample container by said first drive means and said coupling means, and said hand member is activated to hold and lift said sample container by said carriage.

* * * * *